United States Patent [19]

Garbe et al.

[11] Patent Number: 4,981,903

[45] Date of Patent: * Jan. 1, 1991

[54] POLYSILOXANE-GRAFTER COPOLYMER TOPICAL BINDER COMPOSITION WITH NOVEL HYDROPHILIC MONOMERS AND METHOD OF COATING THEREWITH

[75] Inventors: James E. Garbe; Smarajit Mitra, both of St. Paul, Minn.

[73] Assignee: Minnesota Mining and Manufacturing Company, St. Paul, Minn.

[*] Notice: The portion of the term of this patent subsequent to Nov. 20, 2007 has been disclaimed.

[21] Appl. No.: 390,226

[22] Filed: Aug. 7, 1989

[51] Int. Cl.$^5$ .................. C08L 41/00; C08F 30/08
[52] U.S. Cl. .................. 524/547; 524/544; 526/279; 526/264; 526/242; 525/288
[58] Field of Search ............ 526/279, 245, 264, 279, 526/303.1, 317.1, 342, 347

[56] References Cited

U.S. PATENT DOCUMENTS 4,693,935 9/1987 Mazurek ..................... 428/352
4,728,571 3/1988 Clemens et al. ............. 428/352

OTHER PUBLICATIONS

U.S. patent application Ser. No. 07/390,228 filed Aug. 7, 1989, entitled "Polysiloxane-Grafted Copolymer Non-Pressure Sensitive Topical Binder Composition and Method of Coating Therewith".

U.S. patent application Ser. No. 07/390,227, filed Aug. 7, 1989, entitled "Polysiloxane-Grafted Copolymer Topical Binder Composition with Novel Fluorochemical Comonomer and Method of Coating Therewith".

Primary Examiner—Joseph L. Schofer
Assistant Examiner—N. Sarofim
Attorney, Agent, or Firm—Donald M. Sell; Walter N. Kirn; Mark A. Litman

[57] ABSTRACT

A novel composition which can serve as a pressure-sensitive or non-pressure sensitive adhesive at room temperature (20° C.) and which comprises a vinyl polymeric backbone with grafted pendant siloxane polymeric moieties. Also disclosed are topical binder compositions containing the novel composition.

14 Claims, No Drawings

POLYSILOXANE-GRAFTER COPOLYMER TOPICAL BINDER COMPOSITION WITH NOVEL HYDROPHILIC MONOMERS AND METHOD OF COATING THEREWITH

TECHNICAL FIELD

This invention relates to adhesives, surface modifying compositions, sealing compositions, and topical binder compositions comprising a copolymer having a vinyl polymeric backbone with grafted pendant siloxane polymeric moieties and especially to a method of topically applying such coating to animals.

BACKGROUND ART

Pressure sensitive adhesives and adhesive-coated sheet materials are well-known in the art as having the ability to adhere to adhesive-receptive surfaces on mere contact. Such coated sheets in the form of labels and tapes, for example, can be adhered to various substrates under very light "finger pressure" and can later be removed therefrom by stripping the sheet from the surface to which it is attached. It is often desirable to reduce the initial affinity of a PSA for a substrate while still maintaining sufficient ultimate adhesion (after pressure bonding). The prior art has attempted to achieve this result in various ways, mainly by use of different types of "physical spacers" which have been mixed with or coated on the surface of the PSA. Such spacers act to hold the adhesive slightly away from the substrate surface until the desired placement has been achieved. For example, U.S. Pat. Nos. 3,314,838, 3,331,729, and 3,413,168, all assigned to the present assignee, disclose the use of hollow, spheroidal particles or microballoons composed of glass, urea- or phenol-formaldehyde resins, etc., to decrease initial adhesion and thereby provide positionability. The microballoons are described as being crushable or collapsible under applied hand pressure, thereafter enabling the PSA to contact and adhere to the surface of the substrate. Fragments of the collapsed or crushed microballoons may, however, remain on the bonding surface of the adhesive rather than completely dispersed into the adhesive layer, and this may, at least initially, adversely affect the adhesion strength.

Silicone has also been used as a spacing material to reduce the initial adhesion of PSA coatings and thereby produce positionable products. For example, U.S. Pat. No. 3,554,835 (Morgan Adhesives Company) discloses a method of making and using a "slidable" PSA-coated laminate which relies upon "dots" of silicone or other conventional release material as non-adhesive spacers to enable initial positioning of the laminate on a substrate. Similarly, United Kingdom Pat. No. 1,541,311 (United Merchants and Manufacturers, Inc.) describes a PSA-coated laminate where positionability is provided by a uniform and discontinuous surface coating in the form of small beads or droplets of a non-tacky polysiloxane or polysiloxane-polyoxyalkylene block copolymer. Both teachings require an additional manufacturing step or steps to apply the silicone spacing material and to then effect solvent removal, drying, or curing.

In U.S. Pat. No. 4,151,319 (United Merchants and Manufacturers, Inc.) a method for making a positionable PSA-coated laminate is disclosed whereby polysiloxane or polysiloxane-polyoxyalkylene block copolymer is intimately mixed with the PSA itself rather than forming a coating on the PSA surface. "Pre-mixing" of a siloxane polymer or copolymer in a suitable solvent prior to incorporation into the adhesive is recommended. Again, the required mixing or dispersing and the recommended pre-mixing contribute additional process steps. The siloxane additives of this teaching are said to be in the form of small beads or droplets dispersed throughout the adhesive mass, and thus some of the droplets are positioned at the adhesive/release sheet interface of the laminate (i.e., at the PSA surface) and function to allow initial positioning on a substrate. The use of either block copolymers or high molecular weight (above 25,000) polysiloxanes is suggested in United Kingdom Pat. No. 1,541,311 and U.S. Pat. No. 4,151,319 to minimize loss of adhesive mass, but the resultant laminates still may not offer predictable levels of positionability even with minor losses.

U.S. Pat. No. 4,346,189 (Morgan Adhesives Company) describes the use of polysiloxane additives (of up to about 10,000 molecular weight) in a different type of application. The silicones are mixed with tackified, synthetic rubber-based PSA compositions to reduce edge ooze or flow upon cutting of sheets coated with such compositions. Either non-reactive or reactive polysiloxanes can be utilized and are said to appear to adsorb or graft onto other ingredients of the adhesives or take other unknown actions so as to produce the desired effect. It is stated, however, that the silicones can be added even at relatively high concentrations (6 to 10% solids) without adversely affecting the adhesive characteristics of the material.

Graft copolymers, some containing silicone, are being increasingly used for general modification of surface properties, as is described in a series of papers by Y. Yamashita et al., [Polymer Bulletin 7, 289 (1982); Polymer Bulletin 10, 368 (1983); Makromol. Chem. 185, 9 (1984); Macromolecules 18, 580 (1985)]. Such use is also reflected in some recent Japanese art, such as Japanese Pat. Application No. 57-179246, published Nov. 4, 1982, which concerns the use of graft copolymers as additives to impart long-lasting hydrophobicity (or hydrophilicity) to surfaces. In Japanese Pat. Applications Nos. 58-167606, published Oct. 3, 1983, and 58-154766, published Sept. 14, 1983, a method of preparation of silicone graft copolymers and the use of these copolymers in coating compositions such as paint films are described. Here, the copolymers are said to provide long-lasting water- and oil-repellency, stain resistance, and reduced frictional properties. Japanese Pat. Application No. 59-78236, published May 7, 1984, discloses a method of preparing monofunctional polymeric silicone monomers, i.e., macromonomers, for use in the preparation of graft copolymers as surface-treatment agents. The use of such silicone macromonomer-grafted copolymers in coating compositions, again to impart lasting water- and oil-repellency, stain resistance, and low friction characteristics, is described in Japanese Pat. Application No. 59-126478, published July 21, 1984. U.S. Pat. No. 4,728,571 discloses the use of tack-free polysiloxane-grafted copolymers (and blends thereof with other polymeric materials) as release coating compositions for PSA-coated sheet materials and the back side of PSA-coated tapes.

U.S. Pat. No. 4,693,935 teaches polysiloxane-grafted copolymer pressure sensitive adhesive compositions and sheet materials coated therewith. The invention is directed specifically towards pressure sensitive adhesives and articles coated therewith.

SUMMARY OF THE INVENTION

The present invention provides a composition which is pressure-sensitive or non-pressure-sensitive adhesive at room temperature (20.0° C.) and which comprises a copolymer which has pendant polysiloxane grafts. Similar polymers, but with lower Tg's (glass transition temperatures) and different preferred monomers contain the pendant polysiloxane grafts to cause the exposed surface of a layer of the adhesive composition to initially have a lower degree of adhesiveness to provide in effect a temporary "low adhesion frontsize". Upon application, however, the pendant polysiloxane grafts in the prior art (U.S. Pat. No. 4,693,935) appear to migrate into the body of the layer and the adhering surface builds adhesiveness to form a strong adhesive bond. Thus a temporary chemical surface modification of the pressure-sensitive adhesive composition is effected such that positionability of an article bearing the coating of pressure-sensitive adhesive is possible without many of the aforementioned difficulties of the prior art. The present invention, however, can utilize copolymers wherein a slightly different combination and proportion of monomers is selected so that no significant pressure-sensitive characteristics are provided, but the polymers are found to have good topical application binding characteristics, as for finishings to glass, ceramics, metal, and wood as well as for the application of cosmetics and medicaments. The polymers may also be used as sealing compositions for porous materials such as paper and wood.

Chemical incorporation of the polysiloxane into the copolymers of the present invention prevents siloxane loss. Predictable degrees of solubility and bondability are thus reliably achieved for a variety of compositions.

The compositions of this invention comprise a copolymer, the backbone of which has grafted to it monovalent siloxane polymeric moieties having a number average molecular weight above about 500 (preferably from about 500 to about 50,000, most preferably from about 5,000 to about 25,000). If the copolymer has components with Tg's (in their polymerized state) over 20.0° C., the composition can be non-tacky at 20.0° C. and 0.5 Kg/cm$^2$.

More specifically, the composition of the invention comprises the following elements:

(a) a copolymer which comprises repeating A, C, and, B monomers (preferably non-pressure-sensitive compositions wherein the composition has a glass transition temperature of at least 20.0° C., preferably 30.0° C., and most preferably 40.0° C.) and wherein:

A is at least one free radically polymerizable acrylate or methacrylate (hereinafter referred to as "(meth)acrylate") monomer present as 0.1 to 99.9% and for some compositions present as at least 40% of the total weight of the monomers up to 99%;

B is at least one reinforcing monomer copolymerizable with A, the amount by weight of B monomer being present as 0.1 to 99.9% by weight of the monomers and in some cases as at least about 3.0 to a maximum of 30% of the total weight of all monomers; and C is a monomer, present as 0.01 to 50% by weight of all monomers preferably 3 to 30%, having the general formula $X(Y)_n Si(R)_{3-m} Z_m$ wherein X is a vinyl group copolymerizable with the A and B monomers;

Y is a divalent linking group (e.g., alkylene, arylene, alkarylene, and aralkylene of 1 to 30 carbon atoms) and incorporating e.g. ester, amide, urethane, urea groups.

n is zero or 1;

m is an integer of from 1 to 3;

R is hydrogen, lower alkyl (e.g., 1 to 4 carbon atoms, methyl, ethyl, or propyl), aryl (e.g., 6 to 20 carbon atoms, phenyl or substituted phenyl), or alkoxy (preferably lower alkoxy of 1 to 4 carbon atoms);

Z is a monovalent siloxane polymeric moiety having a number average molecular weight above about 500 and is essentially unreactive under copolymerization conditions;

wherein the monomers are copolymerized to form the polymeric backbone with the C monomer grafted thereto;

(b) optionally at least 0.1 up to about 500 parts of a surface conditioner, sealing component, medicament, or skin or hair softening or conditioning ingredient per 10 parts copolymer; and (c) up to about 500 parts of a compatible solvent or plasticizer per 10 parts copolymer.

This invention also provides a process for applying the coating composition to various surfaces such as wood, paper, metal, glass, polymers and animal bodies comprising the application of the composition containing medicaments, conditioning, sealing or softening ingredients to at least a portion of one major surface of a surface or body. The invention also provides specific products comprising the composition with particular classes of additives.

DETAILED DESCRIPTION OF THE INVENTION

The copolymers of the invention have a well-defined structure, having a (meth)acrylic polymeric backbone which has been chemically modified by the addition of a small weight percentage of polysiloxane grafts. When such copolymers are coated on an exposed area of an animal body or on animal hair, non-tacky coatings or localized applications can be aesthetically and comfortably made on those bodies. Once applied to a surface, the composition can maintain the presence of active ingredients applied in the composition.

The surface characteristics of the copolymeric adhesive composition can be chemically tailored through variation of both the molecular weight of the grafted siloxane polymeric moiety and the total siloxane content (weight percentage) of the copolymer, with higher siloxane content and/or molecular weight providing lower initial adhesion. The chemical nature and the molecular weight of the methacrylic polymeric backbone of the copolymer can also be chosen such that the level of adhesion to the substrate can be matched to the requirements of a particular application. Since their siloxane content is relatively low, the copolymers of this invention are readily compatible with siloxane-free polymers, for example polymers of composition similar to that of the vinyl or methacrylic backbone.

The preferred method of preparation of the compositions of this invention provides graft copolymer of high purity which can be coated directly from the polymerization solvent, if necessary or desired. The resultant coatings do not require curing or crosslinking. However, if enhancement of either shear strength or resistance to solvents or photochemical or oxidative forces is desired, crosslinking may be effected by standard methods well-known in the art, such as radiation curing (electron beam or ultraviolet light) or chemical cross-linking.

The siloxane polymeric moieties can be grafted by polymerizing monomer onto reactive sites located on the backbone, by attaching preformed polymeric moieties to sites on the backbone, or, preferably, by copolymerizing the methacrylic monomer(s), A, and, polar monomer(s), B, with preformed polymeric siloxane monomer, C. Since the polymeric siloxane surface modifier is chemically bound, it is possible to chemically tailor the compositions of this invention such that a specific degree of cohesiveness and solubility are provided and can be reproduced with consistency.

As previously mentioned, the composition of this invention comprises a (meth)acrylate copolymer in which monovalent siloxane polymeric moieties having a number average molecular weight above about 500 are grafted to the copolymer backbone. The copolymer preferably consists essentially of copolymerized repeating units from A, B, and C monomers.

The A monomer or monomers (there may be more than one) are chosen such that a non-tacky material is obtained upon polymerization of A (or A and B). Representative examples of A monomers are the lower to intermediate methacrylic acid esters of alcohols such as methanol, ethanol, 1-propanol, 2-propanol, 1-butanol, 1,1-dimethyl ethanol, 2-methyl-1-propanol, 1-pentanol, 2-pentanol, 3-pentanol, 2-methyl-1-butanol, 3-methyl-1-butanol, 2-hexanol, 2-methyl-1-pentanol, 3-methyl-1-pentanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and 1-dodecanol, and the like, the alcohols having from 1 to 12 carbon atoms, preferably 1 to 8 carbon atoms, with the average number of carbon atoms being about 4–12. Some small amount of copolymerizable styrene, vinyl esters, vinyl chloride, vinylidene chloride, acryloyl monomers and the like may be used. Such monomers are known in the art, and many are commercially available. Preferred polymerized A monomer backbone compositions include poly(isooctyl methacrylate), poly(isononyl methacrylate), poly(2-ethylhexyl methacrylate), polyisopentylmethacrylate, poly(n-butyl methacrylate), poly(isobutyl methacrylate), poly(methylmethacrylate), and copolymers thereof with other A monomer or monomers. Some amount of acrylate may also be present, but only in such amounts that these compositions are not pressure sensitive.

The B monomers according to the practice of the present invention are highly polar acrylic and methacrylic monomers. A highly polar monomer as defined in the practice of the present invention are acrylic or methacrylic monomers having at least one highly polarizing group such as hydroxyl(OH), amino (primary, secondary, and tertiary), and ionic groups (e.g., quaternary ammonium, carboxylate salt, sulfonic acid salt, etc.).

The hydrophilic 'B' monomers may be mono- or multifunctional hydroxy group containing molecules represented by the general formula:

$$CH_2=CR^2-CO-L-R^3-(OH)_d$$

where $R^2$=H, methyl, ethyl, cyano or carboxymethyl, L=O, NH, d=1-3 and $R^3$ is a hydrocarbyl radical of valence d+1 containing from 1–12 carbon atoms. The preferred monomers in this class are hydroxyethyl (meth)acrylate, hydroxypropyl (meth)acrylate, hydroxybutyl (meth)acrylate, glycerol mono(meth)acrylate, tris(hydroxymethyl)ethane monoacrylate, pentaerythritol mono(meth)acrylate, N-hydroxymethyl (meth)acrylamide, hydroxyethyl (meth)acrylamide and hydroxypropyl (meth)acrylamide.

The hydrophilic monomer 'B' may belong to the class II of mono- or multifunctional amino group containing molecules of the general formula:

$$CH_2=CR^2-CO-L-R^3-(NR^4R^5)_d$$

where $R^2$, L, $R^3$, and d are as defined above and $R^4$ and $R^5$ are H or alkyl groups of 1–12 carbon atoms or together they constitute a carbocyclic or heterocyclic group. Preferred monomers of this class are aminoethyl (meth)acrylate, aminopropyl (meth)acrylate, N,N-dimethylaminoethyl (meth)acrylate, N,N-diethylaminoethyl (meth)acrylat, N,N-dimethylaminopropyl (meth)acrylamide, N-isopropylaminopropyl (meth)acrylamide and 4-methyl-1-acryloyl-piperazine.

The hydrophilic 'B' monomers may also be alkoxy substituted (meth)acrylates or (meth)acrylamides such as methoxyethyl (meth)acrylate, 2(2-ethoxyethoxy)ethyl (meth)acrylate, polyethylene glycol mono(meth)acrylate or polypropylene glycol mono(meth)acrylate.

Particularly useful are 'B' monomers that have substituted or unsubstituted ammonium groups of the general formula:

$$CH_2=CR-CO-L-R^3-(\overset{\oplus}{N}R^4R^5R^6)_d Q^-$$

where $R^2$, $R^3$, $R^4$, $R^5$, L and d are as defined above, and where $R^6$ is H or alkyl of 1–12 carbon atoms and $Q^-$ is an organic or inorganic anion. Preferred examples of such monomers are 2-N,N,N-trimethylammonium ethyl (meth)acrylate, 2-N,N,N-triethylammonium ethyl (meth)acrylate, 3-N,N,N-trimethylammonium propyl (meth)acrylate, N(2-N',N',N'-trimethylammonium) ethyl (meth)acrylamide, N-(dimethyl hydroxyethyl ammonium) propyl (meth)acrylamide etc. where the counterion may be chloride, bromide, acetate, propionate, laurate, palmitate, stearate etc. The monomer can also be N,N-dimethyl diallyl ammonium salt of an organic or inorganic counterion.

Ammonium group containing polymers can also be prepared by using as the 'B' monomer, any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The hydrophilic 'B' monomers of the invention can also be sulfonic acid group containing monomers e.g. vinyl sulfonic acid, styrene sulfonic acid, 2-acrylamido-2-methyl propane sulfonic acid, allyloxybenzene sulfonic acid etc. These monomers may be used in the protonated acid form as monomers and the corresponding polymers obtained may be neutralized with an organic or inorganic base to give the salt form of the polymers.

The hydrophilic 'B' monomers can be other alkenyl heterocycles such as vinyl imidazoles, vinyl benzimidazoles, vinyl azlactones, vinyl furans etc. These heterocyclic comonomers provide sites for hydrogen bonding with polar substrates and improve adhesion of the resultant polymers to such substrates.

Incorporation of B monomer to the extent of about 2% to about 25% by weight is most preferred and provides compositions of high cohesive or internal strength, good adhesion to polar surfaces and which also retains good physical properties.

The preferred C monomer may be further defined as having an X group which has the general formula $$\begin{array}{cc} R^7 & R^8 \\ | & | \\ CH= & C- \end{array}$$

wherein $R^7$ is a hydrogen atom or a COOH group and $R^8$ is a hydrogen atom, a methyl group, or a $CH_2COOH$ group.

The Z group of the C monomer has the general formula $$R^{10}(-\underset{\underset{R^{11}}{|}}{\overset{\overset{R^9}{|}}{Si}}-O-)_e$$

where $R^9$ and $R^{11}$ are independently lower alkyl, aryl, or fluoroalkyl, where lower alkyl and fluoroalkyl both refer to alkyl groups having from one to three carbon atoms and where aryl refers to phenyl or substituted phenyl (of up to 20 carbon atoms). $R^{10}$ may be alkyl (of 1 to 20 carbon atoms), alkoxy (of 1 to 20 carbon atoms), alkylamino (of 1 to 20 carbon atoms), aryl (of up to 20 carbon atoms), hydroxyl, or fluoroalkyl (of 1 to 20 carbon atoms), and e is an integer from about 5 to about 700. Preferably, the C monomer has a general formula selected from the group consisting of the following, where m is 1, 2, or 3, g is zero or 1, R'' may be alkyl (of 1 to 10 carbon atoms) or hydrogen, f is an integer from 2 to 6, h is an integer from zero to 2, and X, R, and Z are as defined above:

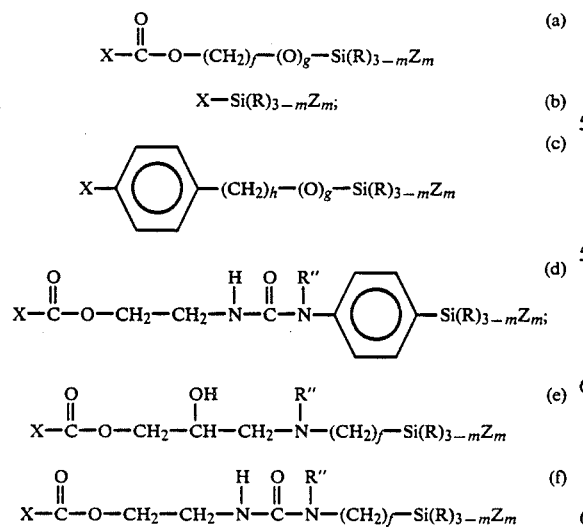

The topical composition of this invention is provided by copolymerizing the A, B and C, and, preferably, B monomers followed, when necessary or desirable, by blending with a compatible cosmetic or medicinally active ingredient in order to optimize the ultimate utile properties of the composition.

When the above described composition is coated on skin or hair in proper proportions in a composition, no tackiness is observed when the composition is dry. Copolymers containing C monomer having a molecular weight less than about 500 are not very effective in providing substantivity, or persistent retention on the skin. Copolymers containing C monomer having a molecular weight greater than 50,000 effectively provide substantivity, but, at such high molecular weights, possible incompatibility of the C monomer with the remaining monomer during the copolymerization process may result in reduced incorporation of C. Molecular weight of C monomer ranging from about 500 to about 50,000 is therefore preferred. A molecular weight range from about 5,000 to about 25,000 is most preferred.

The C monomer is preferably incorporated in the copolymer in the amount of about 0.01 to about 50% of the total monomer weight to obtain the desired properties. The amount of C monomer included may vary depending upon the particular application, but incorporation of such percentages of C monomer having a molecular weight in the above-specified range has been found to proceed smoothly and to result in material which provides effective substantivity for a variety of applications while still being cost effective.

The C monomers of this invention are terminally functional polymers having a single functional group (the vinyl, ethylenically unsaturated, acryloyl, or methacryloyl group) and are sometimes termed macromonomers or "macromers". Such monomers are known and may be prepared by the method disclosed by Milkovich et. al., as described in U.S. Pat. Nos. 3,786,116 and 3,842,059. The preparation of polydimethylsiloxane macromonomer and subsequent copolymerization with vinyl monomer have been described in several papers by Y. Yamashita et al., [Polymer J 14, 913 (1982); ACS Polymer Preprints 25 (1), 245 (1984); Makromol. Chem. 185, 9 (1984)]. This method of macromonomer preparation involves the anionic polymerization of hexamethylcyclotrisiloxane monomer (D₃) to form living polymer of controlled molecular weight, and termination is achieved via chlorosilane compounds containing a polymerizable vinyl group. Free radical copolymerization of the monofunctional siloxane macromonomer with vinyl monomer or monomers provides siloxane-grafted copolymer of well-defined structure, i.e., controlled length and number of grafted siloxane branches.

Suitable monomers for use in the above-mentioned anionic polymerization are, in general, diorganocyclosiloxanes of the formula $$(-\underset{\underset{R^{11}}{|}}{\overset{\overset{R^9}{|}}{Si}}-O-)_e$$

where $R^9$ and $R^{11}$ are as previously defined and where e is an integer of 3 to 7. Preferred are the cyclic siloxanes where e is 3 or 4 and $R^9$ and $R^{11}$ are both methyl, these cyclic siloxanes being hereafter designated D₃ and D₄, respectively. D₃, which is a strained ring structure, is especially preferred.

Initiators of the anionic polymerization are chosen such that monofunctional living polymer is produced. Suitable initiators include alkali metal hydrocarbons such as alkyl or aryl lithium, sodium, or potassium compounds containing up to 20 carbon atoms in the alkyl or aryl radical or more, preferably up to 8 carbon atoms. Examples of such compounds are ethylsodium, propylsodium, phenylsodium, butylpotassium, octylpotassium, methyllithium, ethyllithium, n-butyllithium, sec-butyllithium, tert-butyllithium, phenyllithium, and 2-ethylhexyllithium. Lithium compounds are preferred as initiators. Also suitable as initiators are alkali metal alkoxides, hydroxides, and amides, as well as triorganosilanolates of the formula

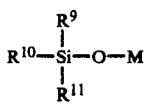

where M is alkali metal, tetraalkylammonium, or tetraalkylphosphonium cation and where $R^9$, $R^{10}$, and $R^{11}$ are as previously defined. The preferred triorganosilanolate initiator is lithium trimethylsilanolate (LTMS). In general, the preferred use of both strained cyclic monomer and lithium initiator reduces the likelihood of redistribution reactions and thereby provides siloxane macromonomer of narrow molecular weight distribution which is reasonably free of unwanted cyclic oligomers.

Molecular weight is determined by the initiator/cyclic monomer ratio, and thus the amount of initiator may vary from about 0.004 to about 0.4 mole of organometallic initiator per mole of monomer. Preferably, the amount will be from about 0.008 to about 0.04 mole of initiator per mole of monomer.

For the initiation of the anionic polymerization, an inert, preferably polar organic solvent can be utilized. Anionic polymerization propagation with lithium counterion requires either a strong polar solvent such as tetrahydrofuran, dimethyl sulfoxide, or hexamethylphosphorous triamide, or a mixture of such polar solvent with nonpolar aliphatic, cycloaliphatic, or aromatic hydrocarbon solvent such as hexane, heptane, octane, cyclohexane, or toluene. The polar solvent serves to "activate" the silanolate ion, making propagation possible.

Generally, the polymerization can be carried out at a temperature ranging from about $-50.0°$ C. to about $100°$ C., preferably from about $-20.0°$ C. to about $30.0°$ C. Anhydrous conditions and an inert atmosphere such as nitrogen, helium, or argon are required.

Termination of the anionic polymerization is, in general, achieved via direct reaction of the living polymeric anion with halogen-containing termination agents, i.e., functionalized chlorosilanes, to produce vinyl-terminated polymeric monomers. Such terminating agents may be represented by the general formula $X(Y)_n Si(R)_{3-m} Cl_m$, where m is 1, 2, or 3 and where X, Y, n, and R have been previously defined. A preferred terminating agent is methacryloxypropyldimethylchlorosilane. The termination reaction is carried out by adding a slight molar excess of the terminating agent (relative to the amount of initiator) to the living polymer at the polymerization temperature. According to the aforementioned papers by Y. Yamashita et al., the reaction mixture may be ultrasonically irradiated after addition of the terminating agent in order to enhance functionality of the macromonomer. Purification of the macromonomer can be effected by addition of methanol.

The copolymerization of the A monomer, B monomer and C monomer is carried out by conventional free radical polymerization such as described by Ulrich, U.S. Pat. No. Re. 24,906. The monomers are dissolved in an inert organic solvent and polymerized utilizing a suitable free radical initiator which can be either thermally or photochemically activated. Suitable thermally activated initiators include azo compounds such as 2,2'-azobis (isobutyronitrile), hydroperoxides such as tert-butyl hydroperoxide, and peroxides such as benzoyl peroxide or cyclohexanone peroxide, and suitable photochemically activated initiators include benzophenone, benzoin ethyl ether, and 2,2-dimethoxy-2-phenyl acetophenone. The amount of initiator used is generally about 0.01 to about 5% by weight of the total polymerizable composition.

The organic solvent used in the free radical copolymerization can be any organic liquid which is inert to the reactants and product and which will not otherwise adversely affect the reaction. Suitable solvents include ethyl acetate and mixtures such as ethyl acetate with toluene or heptane with toluene and isopropyl alcohol. Other solvent systems may also be used. The amount of solvent is generally about 30–80% by weight of the total weight of reactants and solvent. In addition to solution polymerization, the copolymerization can be carried out by other well-known techniques such as suspension, emulsion, and bulk polymerization.

As described above, the preferred grafting technique involves copolymerization of (meth)acrylic monomer, A, reinforcing monomer, B, and chemically tailored macromonomer, C, of controlled molecular weight. Other grafting techniques can be employed, each providing a degree of predictability of the properties of the end product. One alternative technique involves preforming the methacrylic polymeric backbone, then copolymerizing this preformed backbone with cyclic siloxane monomer. Another approach is to graft preformed monofunctional siloxane polymer to a preformed methacrylic polymeric backbone. These and other polymer grafting techniques are described by Noshay and McGrath in *Block Copolymers*, Academic Press, New York (1977), pages 13–16 and in greater detail by Battaerd and Tregear in *Graft Copolymers*, J. Wiley and Sons, New York (1967).

The copolymeric topically applied compositions of this invention in solution or dispersion are easily coated upon suitable body areas but not areas of the primary integumentary system, e.g., hair on the scalp. The compositions maybe used on areas with vestigial hair (such as the face and arms and legs) but are not intended in the practice of the invention as primary treatments for hair. They are also not preferred for treatments in the lining of the eye or nasal passage. Non-mucosal areas of the body of non-aqueous dwelling mammals are particularly preferred and fur treatments for non-human animals are also preferred (dogs, cats, rabbits, etc.). The compositions with other appropriate additives may be used as adhesives, conditioning treatments for organic or inorganic surfaces, and sealants for wood or paper.

The compositions of this invention may be coated by any of a variety of conventional coating techniques such as wiping, spraying, hand spreading, swab application, and the like.

The topical application of medicaments to the skin has traditionally been done with the application of self-sustaining or self-supporting cohesive articles such as films, tapes, or plasters as a proposed improvement over direct applications of powders, ointments, creams, lotions or the like. It has been felt that these more substantial media provided a longer lasting and more controllable application of medicine to the skin or hair of a mammal. These medical applications suffer from distinct problems of their own, however. All of the films and tapes tend to be uncomfortable as they cannot completely conform with stretching, bending, or wrinkling which the exterior surfaces of bodies undergo during movement. The films, tapes and plasters are not cosmetically acceptable, especially if applied to the face and hands, which are exposed to view. Films and tapes are easily and accidentally removed, in part or in whole, from the skin by inadvertent contact or perspiration occurring under the film or tape. This directly reduces the medical efficiency of the application. Films and tapes can trap moisture against the surface which can be medically disadvantageous and can block oxygen penetration to the surface. The application of thin polymer films will not solve these problems because the films can be readily broken and delivery of the medicine can be interrupted.

It has been found in the present invention that by selecting only appropriate proportions of medicaments and the non-pressure-sensitive adhesive polymeric binders in solutions, emulsions, or dispersions that an extremely effective topical application of medicaments, and skin treatments, and fur of hair treatments for animals other than humans may be performed. The proportions are selected, contrary to conventional wisdom, so that a non-cohesive, non-tacky coating of the binder and medicament is formed on the skin particularly in non-mucosal areas.

Medicaments according to the practice of the present invention are those compounds or materials which have a direct medicinal or neurological effect (excluding alcohols). Materials which have a beneficial activity against the growth, propagation or survival of bacteria, fungi, or viruses or which are antihistamines, antitoxins, anaesthetics, analgesics, antipruritics, vitamins, and antiinflammatants are included in the term medicaments. These materials are well known in the medical art and no exhaustive list is thought to be necessary. Exemplary compounds include hydrocortisone acetate, undecylenic acid, tolnaftate, methyl salicylate, lidocaine, oxytetracycline. HCl, retinoic acid, Minoxidil ®, etc. These medicaments may provide the medicinal activity at the site of application or upon absorption through the skin.

These medicaments are combined in the critical proportions of this invention with the oil compatible non-pressure sensitive adhesives. Pressure-sensitive adhesives are art recognized as a standard class of materials. These are adhesives which in dry (substantially solvent free except for residual solvent) form are aggressively and permanently tacky at room temperature (e.g., 15.0° to 25.0° C.) and firmly adhere to a variety of dissimilar surfaces upon mere contact without the need for more than manual pressure. They require no activation by water, solvent or heat in order to exert a strong adhesive holding force towards such materials as paper, cellophane, glass, wood and metals. They have a sufficiently cohesive holding and elastic nature so that, despite their aggressive tackiness, they can be handled with the fingers and removed from smooth surfaces without leaving a substantial residue (cf. Test Method for Pressure-Sensitive Tapes, 6th Ed., Pressure Sensitive Tape Council, 1953). Pressure-sensitive adhesives and tapes are well known, and the wide range and balance of properties desired in such adhesives has been well analyzed (cf. U.S. Pat. No. 4,374,883; and "Pressure-Sensitive Adhesives" in *Treatise on Adhesion and Adhesives* Vol. 2, "Materials", R. I. Patrick, Ed., Marcel Dekker, Inc., N.Y., 1969). The various materials and compositions useful as pressure-sensitive adhesives are available commercially and are thoroughly discussed in the literature (e.g., Houwink and Salomon, *Adhesion and Adhesives,* Elsevier Publ. Co., Amsterdam, Netherlands, 1967; Handbook of Pressure-Sensitive Adhesive Technology, Donates Satas, Ed., VanNostrand Reinhold Co., N.Y., 1982).

Pressure-sensitive adhesives are generally chemically composed of rubber-resin materials, acrylic resins, polyurethane resins, silicone resins, and the like. Among the various patent literature describing compositions and improvements in pressure-sensitive adhesive formulations are U.S. Pat. No. Re. 24,906; U.S. Pat. Nos. 2,652,351; 3,740,366; 3,299,010; 3,770,708; 3,701,758; 3,922,464; 3,931,087; 4,012,560; 4,077,926; 4,387,172; 4,418,120; 4,629,663; and the like. These classes of rubber resin, acrylic, silicone and polyurethane pressure-sensitive adhesives as well as any other pressure-sensitive adhesives are not generally useful in the present invention. Only non-pressure sensitive adhesives are used in the detailed proportions of the present invention, and non-tacky applications of medicaments are provided. The polymers useful in the present invention are oil compatible (dispersible, swellable, or soluble in organic oils and non-polar solvents) and generally are clearly hydrophobic in their properties.

The molecular weight of the polymers used in the compositions may vary over a broad range. The molecular weight must be suitably large to provide the requisite binding effect. The upper limit is determined only by formulation requirements. As the molecular weight increases, the polymers tend to become too viscous to formulate easily into cosmetically-appealing compositions. Generally, polymers having a Brookfield viscosity between 50 and 100,000 cps and preferably between 500 and 15,000 cps, when measured at 16.6 percent non-volatiles, will be useful in the compositions of the invention.

The compositions of the invention are of three basic types, i.e., oils, water-in-oil and oil-in-water emulsions. The oil formulations are prepared by mixing the oil base, polymer and active ingredient (e.g., medicament) together and warming the mixture with slow agitation to about 140° F. The water phase ingredients, if part of an emulsion formulation, are combined and heated to 180° F. This phase is slowly added to the oil phase ingredients, also at 180° F., and the combination allowed to cool with agitation. The formulations generally contain about 0.5 to 10 percent by weight of the acrylate polymer, with the preferred range being from about 0.5 to 5.0 percent by weight. At levels below 0.25 percent, the polymer is less effective in holding a significant amount of the active ingredient (e.g., medicament) on the skin when the skin is exposed to water. At levels above 10 percent, the formulation generally becomes sticky and develops an unpleasant feeling.

The cosmetic oil base, if any, of the compositions may be solid or liquid, but the entire formulation should be somewhat fluid at skin temperatures for ease of application. Fragrances, fillers, dyes, colorants, preservatives, antioxidants and other such material may be included in minor amounts in the compositions without affecting the substantivity of the composition.

When applied to human skin, these products form films of the medicament on the skin surface. The polymer dispersed therein holds the medicament or chemical treatment onto the skin so that a significantly greater pharmacological or cosmetic benefit is provided than the compositions without the polymer.

As indicated above, the composition to be applied to topical areas of mammals (generally non-water dwelling mammals) comprises 0.25–10% by total weight of polymer, preferably 0.5 to 5 percent by weight, and most preferably 0.5 to 2% by weight of polymer per total weight of composition. The active ingredient or medicament may be present in a broader weight range of 0.1 to 50% by total weight of the composition, preferably 0.25 to 20% by weight, more preferably 0.5 to 10% and most preferably 1 to 3% by weight. The ratio of the polymer to medicament (wt. polymer/wt. medicament) should also be in the range of 1/5 to 1/50 to achieve the benefits of the present invention.

These and other aspects of the invention will be shown in the following non-limiting examples.

EXAMPLES 1–3

Polymerizations of methacryloxypropyl-terminated polydimethylsiloxane macromonomer (PDMS) with N,N-dimethylaminoethyl methacrylate (DEMAEMA) and iso-butyl methacrylate (IBM).

To a mixture of 20 parts of PDMS (MW=20,000), 10–30 parts of DMAEMA and 50–70 parts of IBM in 200–300 part of toluene or ethyl acetate was added 0.05–0.5 parts of azobis(isobutyronitrile) (AIBN). This solution was purged with nitrogen atmosphere. The bottle was heated in an Atlas Launder-O-Meter ® at 60° C. for 36–48 hours and the polymer was recovered by evaporation of solvent under reduced pressure.

| Example | PDMS | DMAEMA | IBM |
|---------|------|--------|-----|
| 1 | 20 | 10 | 70 |
| 2 | 20 | 20 | 60 |
| 3 | 20 | 30 | 50 |

EXAMPLES 4–5

Polymerizations of methacryloxypropyl-terminated polydimethylsiloxane macromonomer (PDMS) with N,N-dimethylaminoethyl methacrylate (DMAEMA) and n-butyl methacrylate (NBM).

To a mixture of 20 parts of PDMS (MW=20,000, 5–20 parts of DMAEMA and 60–75 parts of NBM in 200–300 parts of toluene or ethyl acetate was added 0.05–0.5 parts of azobisisobutyronitrile (AIBN). This solution was purged with nitrogen and sealed in a bottle under a nitrogen atmosphere. The bottle was heated in a Launder-O-Meter ® at 60° C. for 36–48 hours and the polymer was recovered by evaporation of solvent under reduced pressure.

| Example | PDMS | DMAEMA | NBM |
|---------|------|--------|-----|
| 4 | 20 | 20 | 60 |
| 5 | 20 | 5 | 75 |

EXAMPLES 6–8

Polymerizations of methacryloxypropy)-terminated polydimethylsiloxane macromonomer (PDMS) with N,N-dimethylaminoethyl methacrylate (DMAEMA), 2-ethylhexyl methacryalte (EHM) and iso-butyl methacrylate (IBM).

To a mixture of 20 parts of PDMS (MW - 20,000), 15–25 parts of DMAEMA, 10 parts of EHM and 45–55 parts of IBM in 200–300 parts of toluene or ethyl acetate was added 0.05–0.5 parts of azobis(isobutyronitrile) (AIBN). This solution was purged with nitrogen and sealed in a bottle under a nitrogen atmosphere. The bottle was heated in a Launder-O-Meter ® at 60° C. for 36–48 hours and the polymer was recovered by evaporation of solvent under reduced pressure.

| Example | PDMS | DMAEMA | EHM | IBM |
|---------|------|--------|-----|-----|
| 6 | 20 | 15 | 10 | 55 |
| 7 | 20 | 20 | 10 | 50 |
| 8 | 20 | 25 | 10 | 45 |

EXAMPLE 9

Polymerizations of methacryloxypropyl-terminated polydimethylsiloxane macromonomer (PDMS) with 2-hydroxyethyl methacrylate (HEMA) and isobutyl methacrylate (IBM).

To a mixture of 20 parts of PDMS (MW=20,000), 20 parts of HEMA and 60 parts of IBM in 200 parts of ethyl acetate was added 0.5 parts of benzoyl peroxide and 10 parts of isopropanol. This solution was purged with nitrogen and sealed in a bottle under a nitrogen atmosphere. The bottle was heated in a Launder-O-Meter ® at 60° C. for 48 hours and the polymer was recovered by evaporation of solvent under reduced pressure.

EXAMPLE 10

Polymerizations of methacryloxypropyl-terminated polydimethylsiloxane macromonomer (PDMS) with ethyl cyanoacrylate (ECA) and isobutyl methacrylate (IBM).

To a mixture of 20 parts of PDMS (MW=20,000) and 60 parts of IBM was added 20 parts of ECA. This mixture immediately began to polymerize and on allowing to stand at room temperature for 4–6 hours had completely solidified to a polymeric mass. The polymer was recovered by evaporation of all volatiles under reduced pressure.

EXAMPLES 11–12

Polymerizations of methacryloxypropyl-terminated polydimethylsiloxane macromonomer (PDMS) with acrylic acid (AA), N,N-dimethylaminoethyl methacrylate (DMAEMA) and n-butyl methacrylate (NBM).

To a mixture of 20 parts of PDMS (MW=20,000) 2–5 parts of AA, 5 parts of DMAEMA and 70–73 parts of NBM in 200 parts of ethyl acetate was added 0.5 parts of benzoyl peroxide. This solution was purged with nitrogen and sealed in a bottle under a nitrogen atmosphere. The bottle was heated in a Launder-O-Meter-®at 60° C. for 36–48 hours and the polymer was recovered by evaporation of solvent under reduced pressure.

| Example | PDMS | DMAEMA | AA | NBM |
|---------|------|--------|----|----|
| 11 | 20 | 5 | 2 | 73 |
| 12 | 20 | 5 | 5 | 70 |

We claim:
1. A composition comprising:
(a) a copolymer which comprises repeating A, B, and C monomers wherein:
A is at least one free radically polymerizable acrylic or methacrylic monomer present in 0.1-99.9% by weight of all monomer present;
B is at least one highly polar acrylic or methacrylic monomer copolymerizable with A and different from A, the amount by weight of B monomer being from 0.1 to 99.9% of the total weight of all monomers in said copolymer; and
C is a monomer present as from 0.01 to 50% by weight of all monomer present and having the general formula

$$X(Y)_n Si(R)_{3-m} Z_m$$

wherein:
X is a vinyl group copolymerizable with the A and B monomers;
Y is a divalent linking group;
R is hydrogen, lower alkyl, aryl, or alkoxy;
Z is a monovalent siloxane polymeric moiety having a number average molecular weight of at least about 500 and is essentially unreactive under copolymerization conditions;
n is zero or 1;
m is an integer of from 1 to 3; and
(b) from 0 to about 500 parts by weight of compatible solvent or plasticizer per 10 parts copolymer.

2. The composition of claim 1 wherein said A monomer is a methacrylic or acrylic acid ester of an alcohol having from 1 to 18 carbon atoms with the average number of carbon atoms being about 4 to 12.

3. The composition of claim 2 wherein the average number of carbon atoms in A is about 6 to 10.

4. The composition of claim 1 wherein said B is a mono-or multifunctional hydroxy group containing molecules represented by the general formula:

$$CH_2=CR^2-CO-L-R^3-(OH)_d$$

where $R^2$=H, methyl, ethyl, cyano or carboxymethyl, L=O,NH, d=1-3 and $R^3$ is a hydrocarbyl radical of valence d+1 containing from 1-12 carbon atoms.

5. The composition of claim 1 wherein said B monomer comprises about 2% to about 15% by weight of all monomers in said copolymer.

6. The composition of claim 1 wherein said X group of said C monomer has the general formula $$\begin{array}{cc} R^7 & R^8 \\ | & | \\ CH= & C- \end{array}$$

wherein $R^7$ is hydrogen or a COOH group and $R^8$ is hydrogen, a methyl group, or a $CH_2COOH$ group.

7. The composition of claim 1 wherein said Z group of said C monomer has the general formula $$R^{10}(-\underset{\underset{R^{11}}{|}}{\overset{\overset{R^9}{|}}{Si}}-O-)_e$$

wherein:
$R^9$ and $R^{11}$ are independently lower alkyl, aryl, or fluoroalkyl;
$R^{10}$ is alkyl, alkoxy, alkylamino, aryl, hydroxyl, or fluoroalkyl; and
e is an integer from about 5 to about 700.

8. The composition of claim 1 wherein said C monomer has a general formula selected from the group consisting of (a) $$X-\overset{\overset{O}{\|}}{C}-O-(CH_2)_f-(O)_g-Si(R)_{3-m}Z_m;$$

(b) $$X-Si(R)_{3-m}Z_m;$$

(c) $$X-\langle\bigcirc\rangle-(CH_2)_h-(O)_g-Si(R)_{3-m}Z_m;$$

(d) $$X-\overset{\overset{O}{\|}}{C}-O-CH_2CH_2-\overset{\overset{H}{|}}{N}-\overset{\overset{O}{\|}}{C}-\overset{\overset{R''}{|}}{N}-\langle\bigcirc\rangle-Si(R)_{3-m}Z_m;$$

(e) $$X-\overset{\overset{O}{\|}}{C}-O-CH_2-\overset{\overset{OH}{|}}{CH}-CH_2-\overset{\overset{R''}{|}}{N}-(CH_2)_f-Si(R)_{3-m}Z_m; \text{ and}$$

(f) $$X-\overset{\overset{O}{\|}}{C}-O-CH_2-CH_2-\overset{\overset{H}{|}}{N}-\overset{\overset{O}{\|}}{C}-\overset{\overset{R''}{|}}{N}-(CH_2)_q-Si(R)_{3-m}Z_m$$

wherein
R'' is alkyl or hydrogen;
m is 1, 2 or 3;
g is zero or 1;
f is an integer from 2 to 6;
h is an integer from 0 to 2.

9. The composition of claim 1 wherein the molecular weight of said C monomer is in the range of about 500 to about 50,000.

10. The composition of claim 1 wherein the molecular weight of said C monomer is in the range of about 5,000 to about 25,000.

11. The composition of claim 1 wherein the amount by weight of said C monomer is within the range of about 0.01 to about 50% of the total monomer weight in said copolymer.

12. The composition of claim 1 wherein the amount by weight of said B plus C monomers is within the range of about 5 to about 60% of the total weight of all monomers in said copolymer.

13. The composition of claim 1 further characterized by being crosslinked.

14. The composition of claim 1 wherein said B monomer comprises a compound of the formulae:

$$CH_2=CR^2-CO-L-R^3-(NR^4R^5)_d$$

or

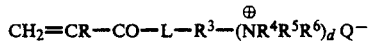
wherein:
R$^2$ is H, methyl, ethyl cyano or carboxymethyl,
L is oxygen or —NH—,
d is 1, 2 or 3,
R$^3$ is a hydrocarbyl radical of valence (d+1) having 1-12 carbon atoms,
R$^4$ and R$^5$ are independently H, alkyl groups of 1-12 carbon atoms, or together constitute a carbocyclic or heterocyclic group,
R$^6$ is H or alkyl group of 1-12 carbon atoms, and
Q$^-$ is an anion.
* * * * *

UNITED STATES PATENT AND TRADEMARK OFFICE
CERTIFICATE OF CORRECTION

PATENT NO. : 4,981,903

DATED : January 1, 1991

INVENTOR(S) : James E. Garbe; Smarajit Mitra

It is certified that error appears in the above-identified patent and that said Letters Patent is hereby corrected as shown below: ON TITLE PAGE:

In the title, "Polysiloxane-Grafter" should read --Polysiloxane-Grafted--.

Signed and Sealed this

Twenty-first Day of July, 1992

Attest:

DOUGLAS B. COMER

Attesting Officer     Acting Commissioner of Patents and Trademarks